United States Patent
Jesch

(10) Patent No.: US 6,916,322 B2
(45) Date of Patent: Jul. 12, 2005

(54) BONE CUTTER DEVICE

(75) Inventor: Wolfgang Jesch, Mauerbach (AT)

(73) Assignee: Degussa Dental GmbH, Hanau (DE)

( * ) Notice: Subject to any disclaimer, the term of this patent is extended or adjusted under 35 U.S.C. 154(b) by 17 days.

(21) Appl. No.: 10/203,638

(22) PCT Filed: Feb. 22, 2001

(86) PCT No.: PCT/EP01/02015

§ 371 (c)(1),
(2), (4) Date: Sep. 12, 2002

(87) PCT Pub. No.: WO01/62179

PCT Pub. Date: Aug. 30, 2001

(65) Prior Publication Data

US 2003/0022132 A1 Jan. 30, 2003

(30) Foreign Application Priority Data

Feb. 25, 2000 (AT) .......................................... A 303/2000

(51) Int. Cl.⁷ ............................. A61B 17/00; A61C 3/02
(52) U.S. Cl. ........................................ 606/80; 433/165
(58) Field of Search ................................ 433/165, 166; 606/80, 96; 408/72 R, 208

(56) References Cited

U.S. PATENT DOCUMENTS

| 1,216,683 A | * | 2/1917 | Greenfield | 433/165 |
| 1,333,388 A | * | 3/1920 | Chester | 433/165 |
| 5,676,545 A | * | 10/1997 | Jones | 433/165 |
| 5,810,828 A | * | 9/1998 | Lightman et al. | 606/80 |
| 6,110,178 A | | 8/2000 | Zech et al. | 606/96 |
| 6,179,615 B1 | * | 1/2001 | Blacklock et al. | 433/165 |

FOREIGN PATENT DOCUMENTS

| DE | 198 01 181 | 7/1999 |
| FR | 2749158 | 12/1997 |
| JP | 5-293124 | 11/1993 |

* cited by examiner

Primary Examiner—John J Wilson
(74) Attorney, Agent, or Firm—Dennison, Schultz, Dougherty & MacDonald

(57) ABSTRACT

Device provided with a bone milling cutter for application on medical, especially dental handpieces. The milling cutter having a milling head is mounted so as to be displaceable in a bushing which is coupled rotation-locking with the milling cutter in the direction of its axis of rotation. A circular knife edge is provided on the face of the bushing, so that the bushing forms a rotating punch, and the milling head can be pushed out of the plane of the face of the bushing.

6 Claims, 2 Drawing Sheets

BONE CUTTER DEVICE

BACKGROUND OF THE INVENTION

The invention relates to a device with a bone milling cutter for applying medical, especially dental handpieces, for example angle pieces.

It has been usual until now when setting the dental implant to separate the mucosa surgically from the jaw bone and to split the periosteum. Thereafter, the implant is inserted into the bone according to manufacturer's directions. The surgical wound is subsequently closed by placing several stitches. Such a procedure has the disadvantage that the mucosa, that is, the gingiva, is traumatically penetrated so that the patient can also suffer from pain in the wound for a long time after the work has been concluded.

SUMMARY OF THE INVENTION

The object of the invention is to obtain the most atraumatic penetration of the gingiva and the periosteum possible, whereby additionally a circular, conical plateau is to be created in the region of the alveolar crest of the upper jaw or the lower jaw.

This objective is accomplished in accordance with the invention in that the milling cutter is mounted so as to be displaceable in a bushing, which is coupled in a rotation-locking manner to the milling cutter in the direction of its axis of rotation, wherein a circular knife edge is provided on the face of the bushing, so that the bushing forms a rotating stamp, and in that the milling head can be pushed out of the plane of the bushing face. In this way, it is achieved that, before the milling head becomes active, the rotating stamp carries out the atraumatic separation of the gingiva and the periosteum, after which the tissue parts that have been cut out are reduced to small pieces, on the one hand, and on the other hand, the corresponding application surface is obtained after an appropriate lowering of the milling head onto the alveolar crest.

Advantageously, the milling cutter can penetrate a bell with its shaft, the bell can be fixedly connected to the milling shaft, and the bushing forming the rotating stamp can be guided so as to slide against the pressure of a spring in the bell, whereby the spring is braced on the bell and on the bushing. In this way, a reliable guidance of the bushing is attained on the exterior of the milling cutter and moreover a part accommodating the spring is also formed. For a secure pick up of the bushing with the rotation of the milling cutter, the shaft of the milling cutter can have a segment with a non-circular (deviating from circular) cross section extending at least over part of its length, which penetrates in a form-locking manner through an opening correspondingly constructed non-circular in the bushing forming the rotating stamp. In an especially advantageous manner, the milling head can have front face cutting edges, which are inclined against the axis of rotation of the milling cutter at an angle differing from 90°, preferably amounting to 60°, by way of which it is achieved that a uniform application surface exists for inserting the implant. Moreover, the cutting edges of the milling head can be constructed on the front face edge of a cutting platelet which has a central axis that coincides with the axis of rotation of the milling cutter, wherein the cutting edges are arranged symmetrically toward the central axis of the cutting platelet and enclose together an angle (0) of preferably 120°, wherein the vertex of the angle lies in the axis of rotation of the milling cutter, through which it is achieved that material detached from the alveolar crest is not pressed into the alveolar opening, but can remain in the intermediate space between the interior partition of the bushing and the rhombi of the cutting platelet.

In order to prevent the bushing from falling off independently over the tip of the milling head, the bushing can be secured, for example, by stops, against a slipping of the milling cutter directed in the direction toward the milling head. Finally, a shoulder can be provided in an especially simple manner as stops on the milling head on its end facing away from the cutting edge on which the projections of the bushing bore hole causing the non-circular cross section get into position, which moreover makes a simple assembly of the device possible.

BRIEF DESCRIPTION OF THE DRAWINGS

An embodiment of the object of the invention is represented in an essentially enlarged scale in the drawing.

DETAILED DESCRIPTION OF THE INVENTION

Figure 4:
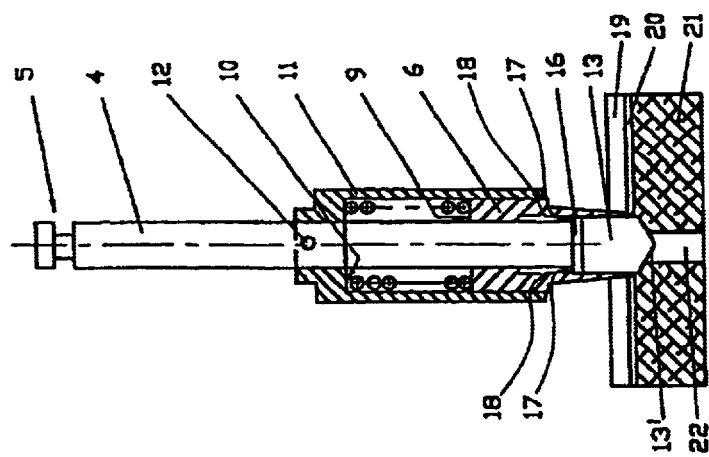
FIG. 4 is a section representation analogous to FIG. 3, but with a completely lowered milling head.

A milling cutter identified with 1, which is comprised by a milling head 2, a shaft element with a non-circular cross section 3, and a shaft element connecting to the same with a round cross section 4, wherein at the free end of the shaft element projecting upward is provided the extension coupling for applying the handpiece or angle piece.

The milling cutter 1 is enclosed in the lower region, and in particular in the region of its milling head 2, and in part also in the region of the shaft element with a non-circular cross section 3, by a bushing 6 whose inner cross section corresponds to the outer cross section of shaft element 3 with a non-circular cross section. This bushing has a face 7 at its free end, which is configured as a circular knife edge, and wherewith the bushing forms a rotating stamp. On the area of the bushing facing away from the face 7 of the same is provided a spring 8 enclosing the shaft area 3, whose one end is braced on an inner face 10 of a cylindrical bell 11, which encloses the bushing outside. This cylindrical bell 11 is locked against rotation and fixedly connected in an axial direction to the round shaft region 4, wherein in the present embodiment a spring pin 12 is provided for fastening.

Via this construction, it is provided that the bushing 6 can be pushed back into the interior of the bell 11, and in particular against the force of the spring 8. The milling head 2, which in the present case is configured as a cutting plate 13, is released by this pushing back, whose front edge 13' is bent and in particular in such a way that the two cutting edges have an angle 0 of about 120° with respect to each other.

Figure 2:
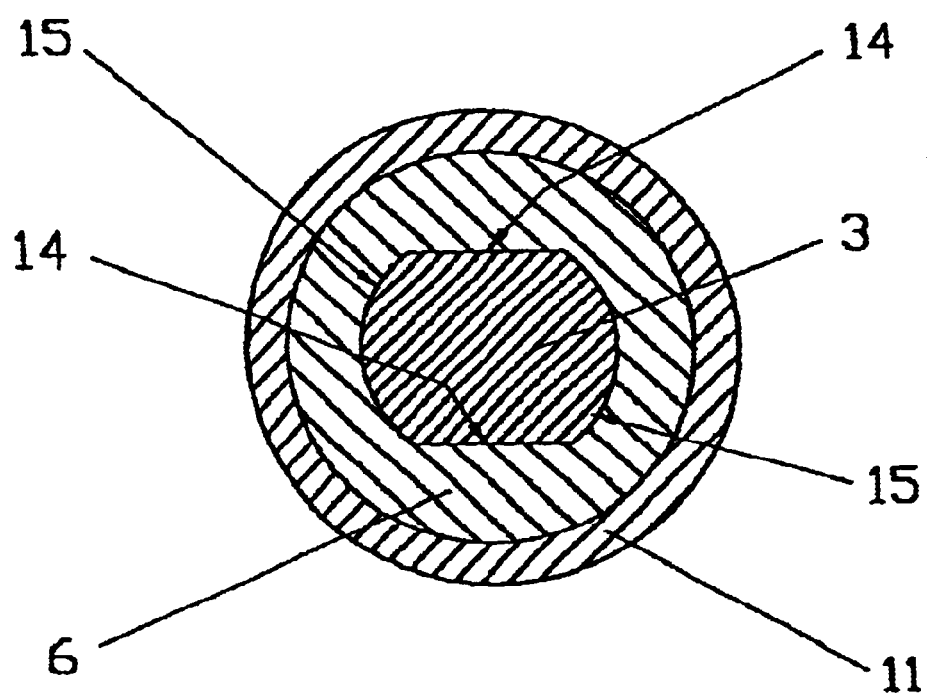
FIG. 2 is a section through line II—II of FIG. 1.

The shaft region 3 with a non-circular cross section here consists of a basically cylindrical element, which is flattened on two flanks lying parallel opposite each other. The flattenings are identified with 14 in FIG. 2. These two flattenings are accordingly then connected to each other with cylinder jacket surfaces 15. These cylinder jacket surfaces 15 serve as guide surfaces for the spring 8.

The milling head has on its region facing away from the cutting edge 13 at the transition to the shaft 3 a collar 16 which possesses shoulders 17 in the region of the flattenings 14 facing away from the cutting plate, which serve as a stop for the projections 18 provided on the interior of the bushing 6. These stops 17, 18 are provided to prevent a slipping of the bushing 6 out of the bell caused by the spring 8.

The gingiva is schematically designated with 19, the periosteum with 20, the alveolar crest with 21, and an alveolus with 22.

Figure 1:
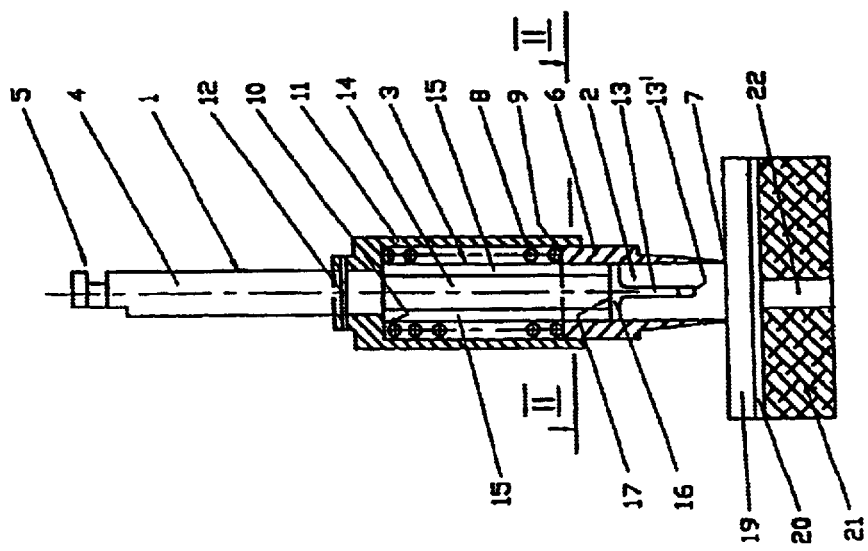
FIG. 1 shows a vertical section through the device.

As stated initially, the object of the invention is reproduced in a very highly enlarged scale. The actual dimensions lie instead in the millimeter range, and indeed the diameter of the bushing 6 in the region of the cutting edge 7 amounts to approximately 3 mm and the overall length of the device when the bushing 6 is completely pushed forward, as shown in FIG. 1, amounts to approximately 33.5 mm. It can therefore be seen that this is a device which must be constructed very small, since otherwise difficulties could arise in the application on the jaw, especially if these implants which are to be inserted in the rear area of the oral cavity.

Figure 3:
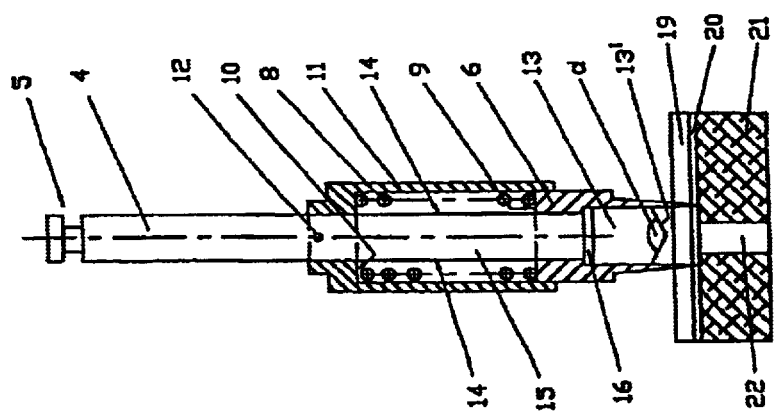
FIG. 3 reproduces a section analogous to FIG. 1, but on a section plane rotated by 90° about the longitudinal axis, and in fact with the gingiva already penetrated, wherein the front cutting edge is seated on the alveolar crest.

When operating the device is, an angle piece or a handpiece is applied to the extension piece 5, whereupon after switching on the motor and setting up the cooling water jet on the cutting knife 7, the apparatus is placed on the gingiva above the alveolus on which the work will be carried out. By means of the rotation of the milling shaft, the bushing 6 is also set into rotation due the non-circular construction of the shaft region 3 and the construction of the interior cross section of the bushing congruent therewith, so that the cutting edge 7 partitions the gingiva and the periosteum under light pressure, that is, congruent holes are punched into these two tissue regions, so that the cutting edge 7 of bushing 6 is then seated on the alveolar crest 21. This condition is reproduced in FIG. 3. With a further downward pressure on the shaft, the bushing 6 is pushed backward in relation to the bell 11 and the tissue material of the gingiva and the periosteum situated in the bushing space is reduced to small pieces by the cutting edge of the milling head 2. This takes place until the cutting plate 13 comes upon the alveolar crest with its front edges 13', and the upper end of the alveolus is so inclined that the alveolar crest has a continuously circular cone-shaped shell surface in the region of the alveolus. An implant drill can then be placed and centered on the cone-shaped shell surface.

Due to the punching out of the region of the gingiva 19 and the periosteum 20 lying above the alveolus 22, an atraumatical removal of these tissue regions takes place, since with the traditional methods, the superfluous tissue parts must be cut off after separating the gingiva from the jaw bone and splitting the periosteum, wherein for separating the gingiva or splitting the periosteum, a larger area of the gingiva must be separated than is necessary with a punching out in accordance with the present invention.

What is claimed is:

1. Device with a bone milling cutter for medical handpieces, comprising:

a milling cutter (1) having a milling head (2) mounted so as is displaceable in a bushing (6) having a borehole with projections (18), said milling cutter having an axis of rotation, said bushing is coupled with the milling cutter (1) in the direction of said axis of rotation, wherein a circular knife edge is provided on the face (7) of the bushing (6), so that the bushing forms a rotating punch, and in that the milling head (2) can be pushed out of the plane of the face (7) of the bushing (6), and wherein the milling cutter (1) with its shaft (3, 4) penetrates through a bell (11), and in that the bell is fixedly connected to the milling cutter shaft (4), and the bushing (6), which forms the rotating punch, is guided so as to slide against the pressure of a spring (8) in the bell (11), whereby the spring (8) is braced on the bell (11) and on the bushing (6).

2. Device according to claim 1, characterized in that the shaft (3, 4) of the milling cutter (1) has a non-circular (deviating from circular) cross section extending at least over part of its length, which penetrates form-locking through a correspondingly non-circularly configured opening in the bushing (6), which forms the rotating punch.

3. Device according to claim 1, characterized in that the milling head (2) has cutting edges (13') on its front face which are inclined against the axis of rotation of the milling cutter (2) at an angle different from 90E, preferably amounting to 60E.

4. Device according to claim 3, characterized in that the cutting edges (13') of the milling head (2) are formed on the front face edge of a cutting platelet (13) which coincides with the axis of rotation of the milling cutter (1), wherein the cutting edges (13') are arranged symmetrically with respect to the central axis of the cutting platelet (13) and together enclose and angle (O) of 120E, wherein the crest of the angle lies in the angle of rotation of the milling cutter.

5. Device according to claim 1, characterized in that the bushing (6) is secured by stops, against a slipping of the milling cutter (1) oriented in the direction toward the milling cutter head (2).

6. Device according to claim 5, characterized in that a shoulder (17) is provided as stops on the milling head (2) on its end facing away from the cutting edge (7) on which the projections (18) of the bushing borehole causing the non-circular cross section get into position.

* * * * *